United States Patent [19]

Manoury et al.

[11] Patent Number: 4,916,133
[45] Date of Patent: Apr. 10, 1990

[54] 1-PIPERAZINYLPYRIMIDINE COMPOSITIONS AND APPLICATION THEREOF IN THERAPEUTICS AND COSMETICS

[75] Inventors: Philippe Manoury, Verrières le Buisson; Jean F. Grollier, Paris, both of France

[73] Assignee: L'Oreal, Paris, France

[21] Appl. No.: 404,551

[22] Filed: Sep. 8, 1989

Related U.S. Application Data

[62] Division of Ser. No. 126,799, Dec. 1, 1987, Pat. No. 4,885,296.

[30] Foreign Application Priority Data

Dec. 1, 1986 [LU] Luxembourg .............................. 86695

[51] Int. Cl.$^4$ ............................................ A61K 31/495
[52] U.S. Cl. .................................... 514/252; 514/880; 544/295
[58] Field of Search ................................ 514/252, 880

[56] References Cited

U.S. PATENT DOCUMENTS 4,532,240  7/1985  Werbel et al. ...................... 514/252
4,729,995  3/1988  Taguchi et al. ..................... 514/252

FOREIGN PATENT DOCUMENTS 0219050  4/1987  European Pat. Off. ............ 514/880
WO86/04231  7/1986  World Int. Prop. O. .......... 514/880

*Primary Examiner*—Glennon H. Hollrah
*Assistant Examiner*—James H. Turnipseed
*Attorney, Agent, or Firm*—Fleit, Jacobson, Cohn, Price, Holman & Stern

[57] ABSTRACT

New 1-piperazinylpyrimidine derivatives, preparation thereof and application thereof in therapeutics and cosmetics.

New compounds derived from 1-piperazinylpyrimidine derivatives, and their application in therapeutics and cosmetics, corresponding to the general formula:

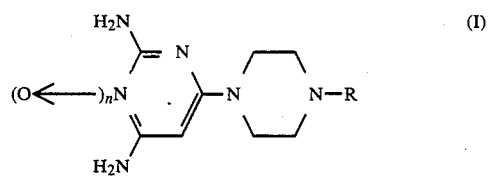

in which R represents an alkoxycarbonyl group containing from 1 to 3 carbon atoms in the alkoxy chain or alternatively a furoyl group, n being 0 or 1, and their addition salts with cosmetically or pharmaceutically acceptable acids.

2 Claims, No Drawings

1-PIPERAZINYLPYRIMIDINE COMPOSITIONS AND APPLICATION THEREOF IN THERAPEUTICS AND COSMETICS

This is a divisional of application Ser. No. 126,799 filed Dec. 1, 1987, now Pat. No. 4,885,296.

The invention relates to new compounds derived from 1-piperazinylpyrimidine and to the application thereof in therapeutics and cosmetics, especially in compositions for inducing and stimulating hair growth and for decreasing hair loss.

Man has a basic number of 100,000 to 150,000 hairs and it is normal to lose 50 to 100 daily. The maintenance of this basic number results essentially from the fact that the life of a hair is subjected to a cycle called pilar cycle during which the hair is formed, it grows and falls before being replaced by a new part which appears in the same follicle.

In the course of a pilar cycle, three successive phases are observed: viz. the anagen phase, the catagen phase and the telogen phase.

During the first phase, referred to as the anagen phase, the hair passes through an active growth period associated with an intense metabolic activity in the bulb region.

The second phase, referred to as the catagen phase, is transitory and it is marked by a slowing down of mitotic activites. During this phase, the hair undergoes an involution, the follicle atrophies and its implantation in the skin appears increasingly shallow.

The final phase, referred to as the telogen phase, corresponds to a rest period for the follicle and the hair finally falls out, pushed by a newly formed anagen hair.

This constant physical renewal process undergoes a natural change during ageing, the hair becomes finer and the cycles thereof become shorter.

Alopecia results when this physical renewal process is accelerated or disturbed, i.e. the growth phases become shorter, the passage of hair into the telogen phase is earlier and hairs fall in larger numbers; the successive growth cycles result in increasingly fine and increasingly short hairs, which are slowly converted into an umpigmented fluff. This phenomenon may lead to baldness.

The pilar cycle depends on many factors capable of leading to a more or less pronounced alopecia. Among these factors, there may be mentioned nutritional factors, endocrinal factors, and nervous factors. The changes in the different categories of hair may be determined with a trichogram, especially a phototrichogram.

Compositions which enable the effect of alopecia to be eliminated or reduced and especially hair growth to be induced or stimulated or hair loss to be reduced have been sought in the cosmetic or pharmaceutical industry for many years.

To this end, compounds such as 6-amino-1,2-dihydro-1-hydroxy-2-imino-4-piperidinopyrimidine and the derivatives thereof have already been proposed. Such compounds are described especially in the patent US-A-4,139,619.

The combination of retinoids with the abovenamed compounds has also been proposed in the patent WO-A-83/02,558.

The Applicant Company has discovered that some 1-piperazinylpyrimidine derivatives could, in a surprising way, induce and stimulate hair growth and decrease their loss.

1-Piperazinylpyrimidine derivatives are already known, especially from the patents US-A-3,644,364 and 3,910,928 and from the article published in Chemical Abstracts 97: 165b.

These compounds are known in particular for their therapeutic properties, especially in the cardiovascular field as antihypertensives.

The Applicant Company has prepared new compounds derived from 1-piperazinylpyrimidine and has discovered that when they were employed in local application, they had a surprising activity on hair regrowth and enabled the growth of the latter to be induced or stimulated and their loss to be decreased.

Therefore, a first subject of the invention consists of new 1-piperazinylpyrimidine derivatives and the preparation thereof.

Another subject of the invention consists of a therapeutic or cosmetic composition which enables, in particular, hair growth to be induced and stimulated and their loss to be decreased.

Another subject of the invention consists of the use of these compounds in the preparation of a composition having a therapeutic effect with regard to the induction and the stimulation of hair growth.

Other subjects of the invention will become apparent on reading the description and the examples which follow.

The new compounds of the invention correspond to the general formula I:

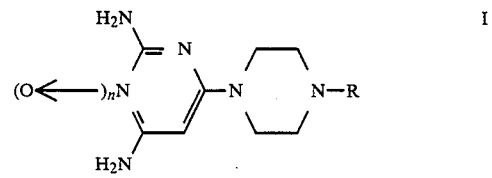

in which R represents an alkoxycarbonyl group containing from 1 to 3 carbon atoms in the alkoxy chain, or alternatively a furoyl group and n is 0 or 1. In the case where n=1, the compounds may optionally be in the tautomeric form, one of the hydrogen atoms of an amino group in position 2 or 4 migrating towards the oxygen atom, according to the following scheme:

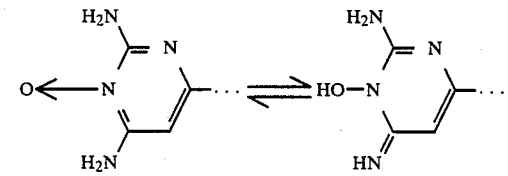

The invention also includes the addition salts that these compounds may form with pharmaceutically or cosmetically acceptable acids.

According to the invention, these compounds may be prepared according to the reaction scheme below.

An optionally N-oxidized pyrimidine of formula II in which X represents a halogen atom, preferably chlorine, is reacted with a piperazine of formula III in which R has the meaning given above, in the heated state and optionally in the presence of a solvent such as chlorobenzene. The acid HX which is also formed during this condensation enables the addition salt of a compound of formula I to be obtained directly.

Scheme

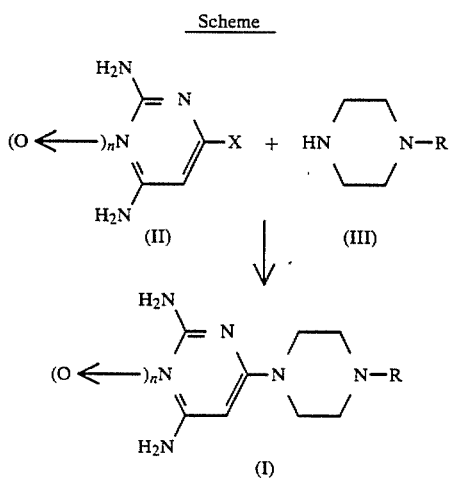

The composition according to the invention is essentially characterized in that it contains, in a pharmaceutically or cosmetically acceptable medium, at least one compound corresponding to formula I above, as well as its addition salts with pharmaceutically or cosmetically acceptable acids.

The particularly preferred compounds which can be used according to the invention are those corresponding to formula (I) in which n=0 and R represents an ethoxycarbonyl or 2-furoyl group or alternatively n=1 and R represents an ethoxycarbonyl group.

There may be mentioned, in particular, ethyl 4-(2,4-diamino-3-oxy-6-pyrimidinyl)piperazinecarboxylate, ethyl 4-(2,4-diamino-6-pyrimidinyl)piperazinecarboxylate, 4-(2,4-diamino-6-pyrimidinyl)-1-(2-furoyl)piperazine and especially their hydrochlorides.

The compositions for local application according to the invention contain the compound of formula (I) in proportions of between 0.01 and 15% by weight relative to the total weight of the composition and preferably between 0.1 and 10% by weight.

A particularly preferred composition is that containing the monohydrochloride of alkyl 4-(2,4-diamino-6-pyrimidinyl)piperazinecarboxylate in proportions of between 0.1 and 5%.

According to an advantageous embodiment of the invention, the compound of formula (I) may be combined with a pyrimidine derivative having an effect on hair regrowth and more particularly 6-amino-1,2-dihydro-1-hydroxy-2-imino-4-piperidinopyrimidine which is also known under the name "Minoxidil", or alternatively a retinoid such as those described in the application WO-82/02,833 or a combination of the two.

Among the particularly preferred retinoids, there may be mentioned, all-trans-retinoic acid and 13-cis-retinoic acid and their physiologically (pharmaceutically or cosmetically) acceptable salts or esters.

These compounds, when they are present, are employed in proportions which may range between 0.01 and 10% by weight for the pyrimidine derivatives and between 0.001 and 2% by weight for the retinoids.

These compounds may be employed in the same composition as the compound of formula (I), or applied separately, either simultaneously or with a time lapse, before or after the composition containing the compound of formula (I).

The compositions according to the invention may be in the form of lotions, emulsions, creams or gels and may optionally be pressurized in the form of an aerosol. They may be applied especially in treatments which employ a composition as defined below, the application of which is followed or not followed by a rinsing, or alternatively in the form of a shampoo.

The cosmetically of pharmaceutically acceptable medium may consist of a thickened or unthickened aqueous, aqueous/alcoholic or alcoholic medium, which may contain one or more cosmetically or pharmaceutically acceptable solvents.

The solvents are preferably chosen from amongst $C_1$–$C_4$ lower alcohols such as ethyl alcohol, isopropyl alcohol and tert-butyl alcohol; alkylene glycols such as propylene glycol and mono- and dialkylene glycol alkyl ethers such as ethylene glycol monoethyl ether, propylene glycol monomethyl ether and diethylene glycol monoethyl ether.

These compositions may contain other adjuvants which are commonly employed in the cosmetic or pharmaceutical field in order to prepare compositions for local application, such as, more particularly, surfactants, thickeners, preservatives and alkalinizing or acidifying agents. The pH of these compositions may vary between 3 and 9 and preferably between 5 and 8.

The thickening or gelling agents, may more particularly be chosen from amongst heterobiopolysaccharides such as, for example, those containing mannose, glucose, glucuronic acid or galacturonic acid units in their chains and more particularly xanthan gums and scleroglucans.

Among these products, there may be mentioned, those marketed under the name KELTROL T or TF, KELZAN S, KELZAN K9C57, KELZAN K8B12 and KELZAN K3B130, marketed by KELCO; the products sold under the name RHODOPOL 23 and 23SC or alternatively RHODIGEL 23 by RHONE POULENC; the product marketed under the name DEUTERON XG by SCHONER GmbH and the products marketed under the name ACTIGUM CX9, CS11 and C56 by CECA/SATIA; other heterobiopolysaccharides which may be employed are described, by way of illustration, in the patent applications EP-A-23,397, UK-A-2,058,106, UK-A-2,058,107, US-A-4,454,316, EP-A-64,354 and DE-A-3,224,547.

Other gelling agents may be chosen from amongst cellulose derivatives such as methylcellulose, hydroxymethylcellulose, carboxymethylcellulose, hydroxybutylcellulose, hydroxyethylcellulose, hydroxypropylcellulose, methylhydroxyethylcellulose and methylhydroxypropylcellulose. These thickening or gelling agents are preferably employed in proportions from 0.5 to 5% and especially from 1 to 3% by weight relative to the total weight of the composition.

However, the thickening agents which may be employed may be chosen from amongst polyacrylic acids crosslinked by a polyfunctional agent, such as the products sold under the name CARBOPOL by GOODRICH or the thickeners resulting from the ionic interaction of a cationic polymer consisting of a celulose copolymer or of a cellulose derivative grafted with a water-soluble quaternary ammonium monomer salt and a carboxylic anionic polymer. Among the latter substances, there may be mentioned, more particularly, the thickeners resulting from the interaction of a copolymer of hydroxyalkylcellulose grafted, by the radical method, with a methacryloylethyl trimethylammonium, methacrylamidopropyl trimethylammonium or dimethyl diallylammonium salt and a carboxylic anionic polymer chosen from amongst the homopolymers of methacrylic acid, the copolymers of methacrylic acid with a monomer chosen from amongst $C_1$–$C_4$ alkyl acrylates or methacrylates, acrylamide derivatives, maleic acid, $C_1$–$C_4$ alkyl monomaleates, vinylpyrrolidone and the copolymers of ethylene and maleic anhydride. The gravimetric ratio between the cationic polymer and the carboxylic anionic polymer is between 1:5 and 5:1.

The thickening agents are employed in proportions of between 0.5 and 2% and preferably between 0.7 and 1.5% by weight relative to the total weight of the composition.

The treatment for the control of hair loss mainly consists in applying to the alopecic regions of the scalp and the hair of an individual, a composition as defined above, for example after washing the scalp and the hair with a shampoo or shortly after shampooing. The preferred method of application consists in applying 1 to 2 g of the composition according to the invention to the alopecic region having a surface area of 200 to 300 cm$^2$ of scalp, at a frequency of 1 to 2 applications per day for 1 to 7 days per week.

The efficacy of the treatment is monitored once a month using a phototrichogram.

The use of the compounds of the formula (I) for the preparation of a composition having an effect of inducing and stimulating hair growth and checking their loss also forms the subject of the invention.

The treatment method has the features of a cosmetic method insofar as it enables the hair and the scalp to be cared for in the cosmetic sense of the term, i.e. to supply them with substances they lack and to beautify them.

Moreover, the method has the features of a therapeutic treatment insofar as the active substance has a therapeutic activity with regard to the biological mechanisms of the pilar cycle.

The following examples are intended to illustrate the invention without, however, being limiting in nature.

EXAMPLES OF PREPARATION 1

Ethyl 4-(2,4-diamino-6-pyrimidinyl)piperazinecarboxylate monohydrochloride.

10 g (0.069 mole) of 6-chloro-2,4-diaminopyrimidine and 21.8 g (0.138 mole) of ethyl piperazine-1-carboxylate are introduced into a conical flask equipped with a magnetic stirrer and a reflux condenser and placed under a nitrogen atmosphere. 75 ml of chlorobenzene are added and the mixture is heated under reflux for 1 hour 30 minutes.

A precipitate is formed, which is filtered in the heated state, rinsed with chlorobenzene and then with ether, and recrystallized in ethanol.

Melting point: 256° C. (ethanol)

Elemental analysis: $C_{11}H_{19}ClN_6O_2$; M=302.76.

|  | C | H | N | O | Cl |
| --- | --- | --- | --- | --- | --- |
| Calculated % | 43.63 | 6.28 | 27.77 | 10.58 | 11.73 |
| Found % | 43.43 | 6.21 | 27.54 | 10.85 | 11.82 |

EXAMPLE OF PREPARATION 2

1-(2,4-diamino-6-pyrimidinyl)-4-(2-furoyl)piperazine monohydrochloride.

A mixture of 4 g (0.0277 mole) of 6-chloro-2,4-diaminopyrimidine, 5 g (0.0277 mole) of 1-(2-furoyl) piperazine and 50 ml of chlorobenzene is heated under reflux for 5 hours.

A precipitate is formed, which is isolated in the heated state by filtration. It is washed with chlorobenzene and then with ether and is recrystallized in methanol.

Melting point: 295° C. (methanol).

Elemental analysis: $C_{13}H_{17}ClN_6O_2$; M=324.5.

|  | C | H | N | O | Cl |
| --- | --- | --- | --- | --- | --- |
| Calculated % | 48.07 | 5.24 | 25.89 | 9.86 | 10.94 |
| Found % | 48.13 | 5.26 | 25.80 | 10.09 | 11.09 |

EXAMPLE OF PREPARATION 3

Ethyl 4-(2,4-diamino-3-oxy-6-pyrimidinyl)-piperazinecarboxylate monohydrochloride.

10 g (0.063 mole) of 6-chloro-3-oxy-2,4-diaminopyrimidine and 30 g (0.190 mole) of ethyl piperazine-1-carboxylate are introduced into a conical flask equipped with a magnetic stirrer and a reflux condenser and placed under a nitrogen atmosphere. The mixture is heated to 100° C. in the course of 1 hour and maintained at this temperature for 1 hour 30 minutes.

Approximately 30 ml of water are added to the hot mixture, the white precipitate formed is separated, it is washed with water and then with ether and it is recrystallized in isopropyl alcohol.

The base thus obtained is dissolved in a minimum of ethanol and an excess of ethereal hydrogen chloride is added to the solution. The hydrochloride preicipitate is separated and is crystallized in ethanol.

Melting point: 215° C. (ethanol)

Elemental analysis: $C_{11}H_{19}ClN_6O_3$; M=318.76.

|  | C | H | N | O | Cl |
| --- | --- | --- | --- | --- | --- |
| Calculated % | 41.48 | 5.96 | 26.35 | 15.06 | 11.13 |
| Found % | 41.48 | 5.95 | 26.28 | 14.87 | 11.21 |

The micro analysis and the IR and NMR spectrum confirm the structure of the compounds obtained in the preparation examples.

EXAMPLE OF FORMULATION 1

A lotion, active on the growth of hair an drecreasing hair loss is prepared:

| Ethyl 4-(2,4-diamino-6-pyrimidinyl) piperazine carboxylate monohydrochloride | 4 g |
| --- | --- |
| Preservative, perfume | qs |
| Ethyl alcohol (70% solution) | qs 100 g |

The activity of the composition for stimulating hair growth is evaluated over a placebo by applying 1 ml of this composition once a day on the alopecic area of the hair scalp of five persons having a mean age of 40 years.

After a treatment of several months, the composition improves efficiently the condition of the hair.

EXAMPLE OF FORMULATION 2

| 4-(2,4-diamino-6-pyrimidinyl)-1-(2-furoyl) piperazine monohydrochloride | 2 g |
| --- | --- |
| Diethyleneglycol monoethyl ether | 20 g |
| Ethyl alcohol | 40,5 g |

| -continued | |
|---|---|
| Water | qs 100,00 g |

This lotion is applied as indicated in example 1 and similar results are noticed.

| EXAMPLES OF FORMULATION | 3 | 4 |
|---|---|---|
| Ethyl 4-(2,4-diamino-3-oxy-6-pyrimidinyl)piperazinecarboxylate monohydrochloride | 3 | 3 |
| Heteropolysaccharide in g AS Keltrol T | 1 | |
| Hydroxypropylcellulose in g AS Klucel G | | 3 |
| Isopropyl alcohol in g | 39.5 | |
| Tert-butyl alcohol in g | | 39.5 |
| Water qs in g | 100 | 100 |

When applied to the alopecic parts of the scalp, these compositions enable an improvement to be observed in the condition of the hair.

EXAMPLE OF FORMULATION 5

A lotion having the following composition is prepared:

| Ethyl 4-(2,4-diamino-6-pyrimidinyl)-piperazinecarboxylate monohydrochloride | 3.00 g |
|---|---|
| Propylene glycol | 20.00 g |
| Ethyl alcohol | 50.00 g |
| Water | qs 100.00 g |

When applied to the alopecic parts of the scalp, this lotion enables the condition of the scalp to be improved.

EXAMPLE OF FORMULATION 6

A lotion having the following composition is prepared:

| Ethyl 4-(2,4-diamino-6-pyrimidinyl)-piperazinecarboxylate monohydrochloride | 2.50 g |
|---|---|
| Minoxidil | 1.00 g |
| Propylene glycol | 20.00 g |
| Ethyl alcohol | 50.00 g |
| Water | qs 100.00 g |

When applied as mentioned in Example 1, to the alopecic part of the scalp, a stimulation of hair regrowth is observed.

EXAMPLE OF FORMULATION 7

A lotion having the following composition is prepared:

| 13-cis-retinoic acid | 0.0125 g |
|---|---|
| Ethyl 4-(2,4-diamino-3-oxy-6-pyrimidinyl) piperazinecarboxylate monohydrochloride | 3.00 g |
| Ethyl alcohol | 95.00 g |
| Propylene glycol | qs 100.00 g |

When applied as mentioned in Example 1, to the alopecic parts of the scalp, a stimulation of hair regrowth is observed.

EXAMPLE OF FORMULATION 8

A gel having the following composition is prepared:

| Trans-retinoic acid | 0.025 g |
|---|---|
| Ethyl 4-(2,4-diamino-3-oxy-6-pyrimidinyl)-piperazinecarboxylate monohydrochloride | 3.00 g |
| Ethyl alcohol | 50.00 g |
| Water | 13.00 g |
| Acrylic acid homopolymer crosslinked by a polyfunctional agent, sold under the name CARBOPOL 940 | 1.00 g |
| Triethanolamine | qs pH = 5 |
| Preservative | qs |
| Propylene glycol | qs 100.00 g |

EXAMPLE OF FORMULATION 9

A lotion having the following composition is prepared:

| Ethyl 4-(2,4-diamino-6-pyrimidinyl)-piperazinecarboxylate monohydrochloride | 3.00 g |
|---|---|
| 13-cis-retinoic acid | 0.0125 g |
| Ethyl alcohol | 95.00 g |
| Propylene glycol | qs 100.00 g |

When applied as mentioned in Example 1 to the alopecic part of the scalp, a stimulation of hair regrowth is observed.

EXAMPLE OF FORMULATION 10

A gel having the following composition is prepared:

| Ethyl 4-(2,4-diamino-6-pyrimidinyl)-piperazinecarboxylate monohydrochloride | 3.00 g |
|---|---|
| Trans-retinoic acid | 0.025 g |
| Ethyl alcohol | 50.00 g |
| Water | 13.00 g |
| Acrylic acid homopolymer crosslinked by a polyfunctional agent, sold under the name CARBOPOL 940 | 1.00 g |
| Triethanolamine | qs pH = 5 |
| Preservative | qs |
| Propylene glycol | qs 100.00 g |

When applied as mentioned in Example 1 to the alopecic part of the scalp, a stimulation of hair regrowth is observed.

We claim:

1. Composition to be used for the treatment of the scalp and hair for inducing and stimulating hair growth and for decreasing hair loss containing an effective amount of a compound of the formula:

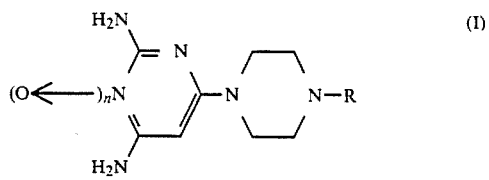

in which R represents an alkoxycarbonyl group having from 1 to 3 carbon atoms in the alkoxy chain or represents a furoyl group, n is 0 or 1, and their acid addition salts, in the form of an aqueous/alcholic gel containing a gelling agent selected from the group consisting of heterobiopolysaccharides and celulose derivatives.

2. Composition to be used for the treatment of the scalp and hair for inducing and stimulating hair growth and for decreasing hair loss containing an effective amount of a compound of the formula:

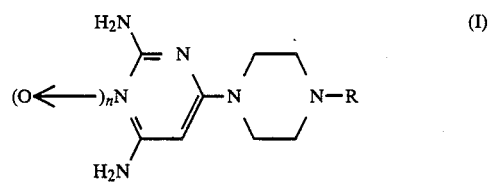

in which R represents an alkoxycarbonyl group having from 1 to 3 carbon atoms in the alkoxy chain or represents a furoyl group, n is 0 or 1, and their acid addition salts, and containing thickeners selected from the group consisting of acrylic acid polymers crosslinked by a polyfunctional agent or thickeners resulting from the ionic inter-action of a cationic polymer consisting of a cellulose copolymer or a cellulose derivative grafted with a water-soluble quaternary ammonium monomer salt and a carboxylic anionic polymer.

* * * * *